United States Patent [19]

Golias et al.

[11] Patent Number: 5,173,265
[45] Date of Patent: Dec. 22, 1992

[54] MANUALLY OPERATED PUMP INSERTER FOR TEST TUBES

[75] Inventors: Tipton L. Golias; Ovay H. Mayes; Robert J. Sarrine, all of Beaumont, Tex.

[73] Assignee: Helena Laboratories Corporation, Beaumont, Tex.

[21] Appl. No.: 720,372

[22] Filed: Jun. 25, 1991

Related U.S. Application Data

[63] Continuation-in-part of Ser. No. 383,339, Jul. 24, 1989, Pat. No. 5,055,271.

[51] Int. Cl.$^5$ .............................................. B01L 9/00
[52] U.S. Cl. ....................................... 422/99; 422/100; 422/103; 422/104; 73/864.23; 73/864.24
[58] Field of Search ................. 422/99, 100, 103, 104; 73/864.24, 864.23, 864.25, 864.11

[56] References Cited

U.S. PATENT DOCUMENTS

| | | | |
|---|---|---|---|
| 3,650,306 | 3/1972 | Lancaster | 422/100 |
| 3,687,175 | 8/1972 | Babey | 422/99 |
| 4,301,116 | 11/1981 | Ida et al. | 422/63 |
| 4,478,094 | 10/1984 | Salomaa et al. | 73/863.32 |
| 4,554,839 | 11/1985 | Hewett et al. | 73/863.32 |
| 4,605,536 | 8/1986 | Kuhnert et al. | 422/99 |
| 4,779,467 | 10/1988 | Rainin et al. | 73/864.17 |
| 4,812,293 | 3/1989 | McLaurin et al. | 422/102 |
| 4,938,929 | 7/1990 | Bost | 422/100 |
| 4,951,512 | 8/1990 | Mazza et al. | 73/864.23 |

Primary Examiner—James C. Housel
Assistant Examiner—Long V. Le
Attorney, Agent, or Firm—Spencer, Frank & Schneider

[57] ABSTRACT

A manually operated apparatus for attaching one or more pump mechanisms to a like number of sealed test tubes, each test tube sealed by a resilient, puncturable closure. The apparatus includes a frame having a base, a support attached to the frame for releasably supporting one or more pump mechanisms, a test tube holder for releasably holding one or more test tubes, the holder movably engaging and being displaceable on the base of the frame into position in alignment with the support, and a manually operated insertion mechanism, attached to the frame, for displacing the support towards the holder (with test tubes therein), to puncture the closure of a test tube with a pump mechanism. Using the apparatus includes placing one or more test tubes having closures into the holder, displacing the holder into position, placing one or more pump mechanisms in the support, and manually activating the insertion mechanism to puncture the one or more closures with the one or more pump mechanisms.

14 Claims, 2 Drawing Sheets

MANUALLY OPERATED PUMP INSERTER FOR TEST TUBES

CROSS-REFERENCE TO RELATED APPLICATION

This is a continuation-in-part application of allowed copending U.S. patent application Ser. No. 07/383,339, filed Jul. 24, 1989, to Tipton L. Golias et al., entitled "PUMP INSERTER FOR TEST TUBES", now U.S. Pat. No. 5,055,271, the disclosure of which is hereby incorporated by reference in its entirety. The present application includes subject matter in common with prior application Ser. No. 07/504,597, filed Apr. 4, 1990, which is a continuation-in-part of application Ser. No. 07/382,760, filed Jul. 21, 1989, which is a continuation-in-part of application Ser. No. 07/208,447 filed Jun. 20, 1988, abandoned, all of which are hereby incorporated by reference in their entireties.

BACKGROUND OF THE INVENTION

The present invention relates to test tubes in general, and more particularly, to a manually operated apparatus for inserting pump mechanisms into test tubes which are sealed by a closure such that the contents of the test tube may be discharged without removing the closure from the test tube.

Heretofore it has been known to provide a resilient closure or rubber stopper for a container and to discharge the contents of the container by using a pump mechanism which establishes inlet and outlet flow paths through the closure. Air pressure through the inlet path pressurizes the interior of the container and causes the contents to flow through the outlet path. Pump mechanisms of this type are, of course, known and, prior to the present invention, the establishing of the fluid flow paths was accomplished by puncturing the closure with a hand-held pump mechanism.

There are, of course, numerous concerns when puncturing the closure of a test tube by hand. A fundamental problem, of course, is that a test tube is formed of glass and, therefore, is subjected to breaking if excessive forces are used.

Equally important is the need to align the direction of force relative to the elongated axis of the test tube to provide proper positioning of the pump mechanism. Furthermore, the amount of force necessary to penetrate or puncture the test tube closure is minimized if the direction of the inserting force is parallel to the longitudinal axis of the test tube rather than at some angle to the longitudinal axis of the test tube.

Yet another problem in connection with attaching pump mechanisms to test tubes by hand is the difficulty in handling such mechanisms because of their relatively small size.

A still further problem is the amount of time and labor involved in attaching pump mechanisms to test tubes if each pump must be attached by hand in sequence, on an individual basis, rather than attaching a plurality of pump mechanisms simultaneously to individual test tubes.

Avoiding contact with the specimen in the tube may also be an important consideration. Insertion of the pump mechanisms by hand may pose a risk of such undesirable contact occurring if test tube breakage should occur.

In allowed copending U.S. patent application Ser. No. 07/383,339, a pump inserter is disclosed for the efficient automatic insertion of a large number of pump mechanisms into test tubes. However, in some circumstances, the use of such an apparatus may not be most efficient or cost effective, such as when only one or a small number of test tubes are involved.

Thus, the inventors recognized that there existed a need for a relatively inexpensive manually operated pump inserter for test tubes.

SUMMARY OF THE INVENTION

It is therefore an object of the invention to provide a manually operated apparatus and method for attaching pump mechanisms to sealed test tubes in an efficient, cost effective manner.

The present invention overcomes the shortcomings and fills the need recognized by the inventors, by providing a manually operated mechanical apparatus and method for inserting one or more pump mechanisms, or parts of pump mechanisms, through test tube closures in a manner that reduces the chance of specimen contact.

The present invention therefore facilitates aseptic handling of samples when protection from sample contact is a concern.

The present invention contemplates insertion of a plurality of pump mechanisms, or parts thereof, simultaneously through the respective closures of a plurality of sealed test tubes.

The present invention also contemplates protecting the individual test tubes from breakage and aligning the test tubes and the pump mechanisms relative to each other such that the force applied to insert the pump mechanism through the test tube closure is aligned along the longitudinal axis of the test tube, thereby minimizing the amount of force necessary to penetrate the closure and reducing breakage and damage.

The present invention further contemplates a manually operated mechanical apparatus whereby one or more pump mechanisms are placed in a holder and retained in a desired position relative to the test tubes and one or more test tubes may be positioned accurately such that the pump mechanisms may be inserted through the closures of the desired test tubes by the actuation of a handle.

BRIEF DESCRIPTION OF THE DRAWINGS

The foregoing benefits and advantages of the present invention will be more fully understood upon reading the following detailed description of the invention taken in conjunction with the drawings.

In the drawings, wherein like reference numerals identify corresponding components.

DETAILED DESCRIPTION OF THE PREFERRED EMBODIMENT

While the invention is now described with respect to the illustrated embodiment, it should be understood that the scope of the invention is not intended to be limited to the details of this embodiment.

Figure 1:
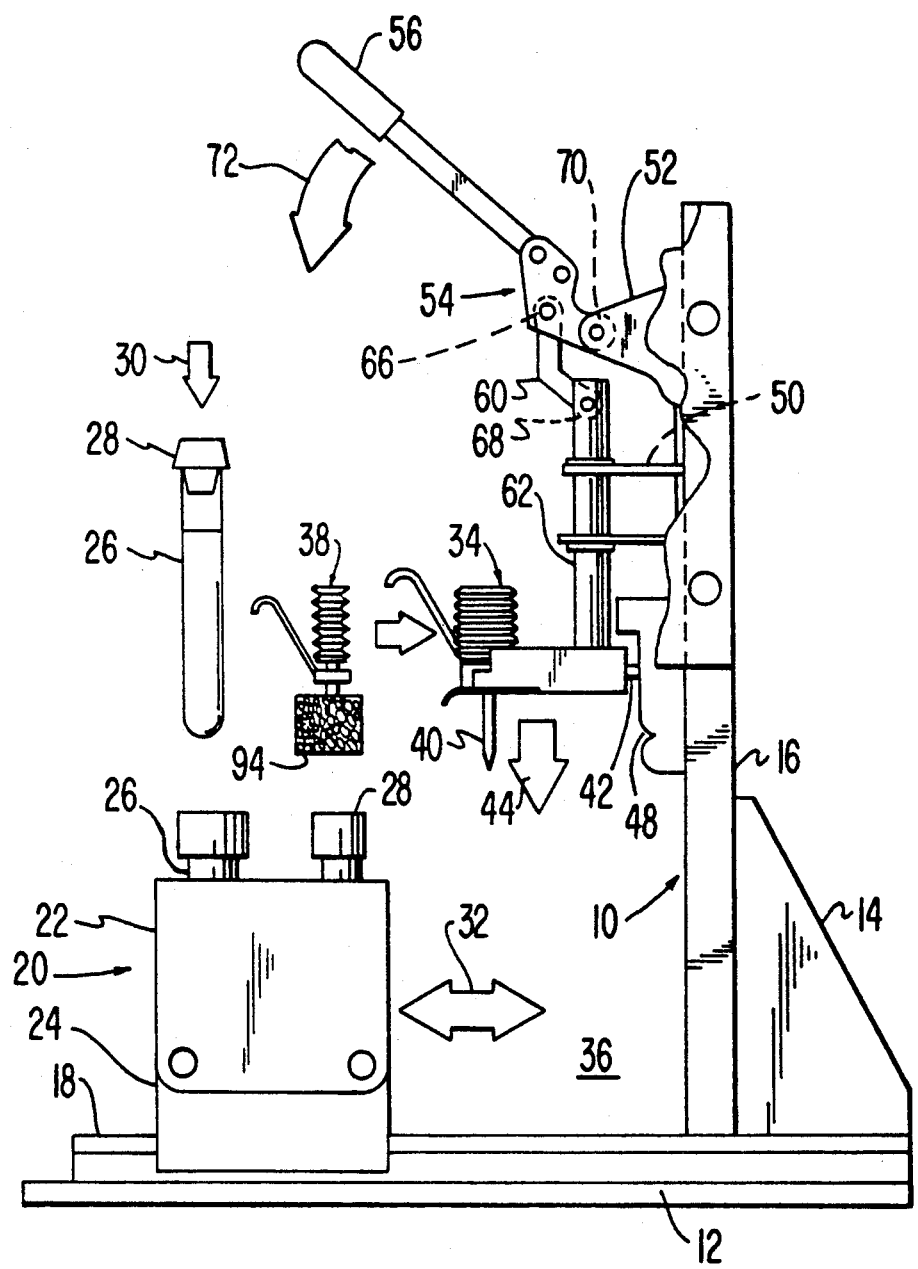
FIG. 1 is a side view, partially broken away, of an apparatus according to the principles of the present invention with pump mechanisms and test tubes illustrated.

Referring to FIG. 1, shown is a side view of an embodiment of the invention having a support frame 10 which includes base 12, brace 14, and vertical frame member 16. The vertical frame member is secured to the base, such as by screws, and the brace 14 is secured in a similar fashion to both the base and the vertical frame member thus providing support for the vertical frame member. A slide bar 18, attached to base 12, is for supporting a slidably mounted test tube holder assembly 20. The test tube holder assembly 20, is comprised of a top piece 22, which is formed as an inverted U-shaped member, and a bottom piece 24, which is formed as a generally rectangular block. The test tube holder assembly receives and holds one or more test tubes 26 of various sizes, each of which is sealed by a resilient, self-sealing, reusable, puncturable cap or stopper 28 as is conventional. Each of the test tubes are placed in holder assembly 20 from above, (i.e. vertically) as shown by arrow 30. The test tube holder top piece 22 includes a plurality of apertures to receive the test tubes therethrough. The test tube holder assembly 20 is slidably removable from slide bar 18 at one end of the slide bar 18 opposite from the vertical frame member 16. Test tube holder assembly 20 may be slid manually, forward and back, on slide bar 18 as shown by the double arrow 32. In operation, the test tube holder assembly 20 with one or more test tubes 26 placed therein, is slid into position underneath a pump support assembly 34 at a first station 36 for insertion of pump mechanisms 38, as will be described more fully in connection with the explanation of the present invention. Each pump mechanism includes one or more barbs or needles 40 for puncturing the cap of the sealed test tube.

Pump support assembly 34, which includes a rearwardly extending (i.e., toward vertical frame member 16) adjustment screw 42, is moveable vertically as shown by arrow 44 parallel to vertical frame member 16, relative to a pair of spaced apart, notched alignment members 46 which alignment members are secured to the vertical frame member. Pump support assembly 34 receives and removably supports one or more pump mechanisms 38. Test tubes 26 in holder assembly 20 and pump mechanisms 38 in pump support assembly 34 are vertically aligned relative to each other such that pump mechanisms may be inserted into the test tubes through the test tube closure or cap 28. The insertion of the pump mechanisms through the test tube closures occurs at a first station 36.

A horizontal support 50 is attached through a bifurcated support 52 to the vertical frame member 16. A manually activated pump insertion mechanism 54 which includes, generally, a handle 56 mounted to a handle bracket 58, which is connected by a strut 60 to a vertically reciprocable rod 62, is mounted in the support 52. Support 50 is of a generally U-shaped configuration with upper and lower spaced apart planar legs, and part of the bifurcated support 52 is positioned between the planar legs of horizontal support 50. Pump insertion mechanism 54 is partially enclosed in a cover 64, which is illustrated in partially cutaway form in FIG. 1. Rod 62 is slidably positioned in holes in the legs of U-shaped support 50 so that rod 62 moves vertically up and down parallel to vertical frame member 16 when the handle 56 is pivoted by being pushed or pulled by the operator, respectively. Strut 60, attached to handle bracket 58, transfers the force applied to handle 56 to move the rod 62. Handle bracket 58 and strut 60 are pivotally connected together at a first joint 66, and strut 60 and rod 62 are pivotally connected together at a second joint 68. Handle bracket 58 is movably connected to support 52 at a third joint 70.

When handle 56 is pulled, pivoting about third joint 70 as shown by arrow 72, rod 62 moves downward thereby pushing pump support assembly 34 downwardly. Thus, when one or more test tubes 26 in test tube holder assembly 20 are positioned at the first station 36 directly under a pump mechanism 38, the pump mechanism is moved downwardly and the barb or needle 40 punctures the closure 28 of a test tube thereby attaching a pump mechanism 38 to a test tube.

After insertion of a pump mechanism to a test tube, the handle 56 is then pushed back a short distance such that the pump support assembly moves upwardly to a first detent position defined by rearwardly extending screw bearing against notches 48 in the alignment members 46, thus removing the pressure placed on the closure 28 by pump mechanisms 38 and needles 40 via rod 62 and pump support assembly 34. The test tube holder assembly 20 may now be slid horizontally along slide bar 18, away from vertical support member 16, and a test tube 26 with a pump mechanism 38 inserted may be removed from test tube holder assembly 20.

Figure 2:
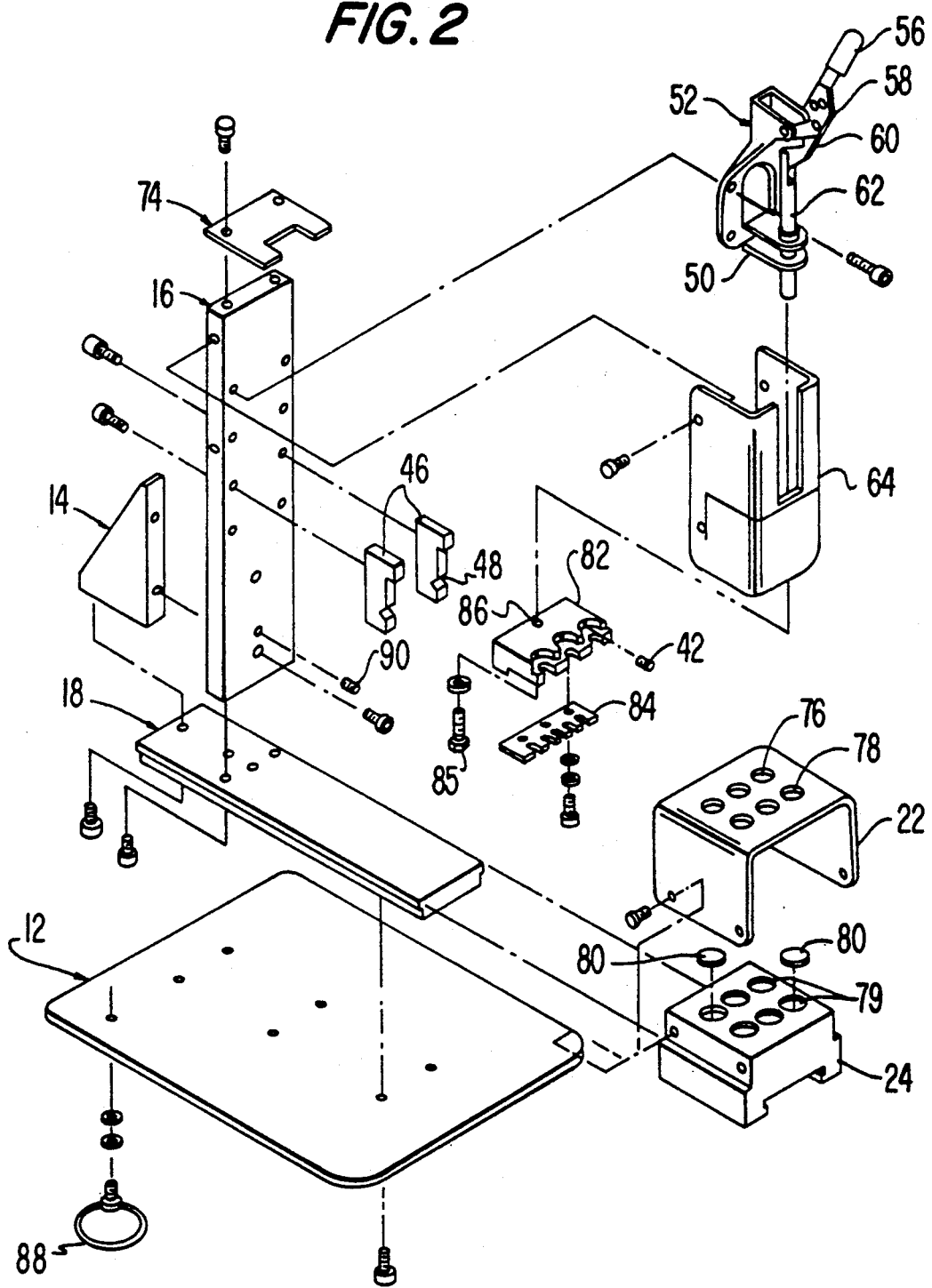
FIG. 2 is an exploded perspective view, illustrating the apparatus of the present invention from the opposite direction relative to FIG. 1.

Referring now to FIG. 2, shown is an exploded view of the embodiment of the invention of FIG. 1. The insertion mechanism 54, is partially enclosed in a front cover 64 and a top cover 74, both of which are secured to the vertical frame member 16. Test tube holder assembly 20 includes a plurality of holes in the test tube holder top piece 22 to receive test tubes of different diameters and, in the illustration of FIG. 2, the holes for receiving test tubes are configured in two rows of three holes per row.

As shown, there are six holes in two rows of three holes each. The first row (in the direction closer to the vertical frame member) includes larger diameter holes 76 and the second row includes smaller diameter holes 78. Providing holes 76 and 78 of different diameters accommodates test tubes of different sizes and thus the present invention may be utilized with test tubes of two standard diameters, for example, 13 mm and 16 mm. Other combinations of diameters could be provided for within the scope of the invention.

The bottom portion 24 of test tube holder assembly 20 may include a plurality of holes 79, aligned under the holes 76, 78 in the top portion 22 of the test tube holder assembly. Preferably foam cushion members 80 are provided on the bottom part of the test tube holder assembly to provide support for the bottom of the test tube and thus minimize opportunities for breakage especially when the vertical force along the longitudinal axis of the test tubes is applied to insert the pump mechanism into the test tube.

The pump mechanisms are provided with their needles 40 inserted into Styrofoam or the like to protect persons handling the pump mechanisms against accidental injury. The pump support assembly 34 includes pressure bar 82 and web 84 for securely holding pump mechanisms 38. The pressure bar and web assembly includes, in the illustrated embodiment, three semicircular recesses for accommodating three pump mechanisms. When the pump mechanisms are positioned in the pressure bar and web assembly, the Styrofoam protectors for the pump needles 40 may be manually removed. It should be noted that a screw 85 extends through a hole 86 in pressure bar 82 to engage the rod 62 and to contact the web 84.

Base 12 may include feet 88 to provide firm support for the apparatus on a flat level surface. The feet 88 may be formed as suction pads to provide resistance against movement of the apparatus during operation.

An adjustment screw 90 provides for fine adjustment of the centering of pump mechanisms 38 relative to the test tube closures 28 as follows. Adjustment screw 90 functions as a stop or abutment which limits the sliding movement of the test tube holder assembly toward the vertical frame member 16. Thus by adjusting screw 90 inwardly or outwardly, the abutment or stop position of the test tube holder is adjusted to be aligned under the pump mechanisms. Adjustment screw 42 is adjusted to provide a good positive detent against notches 48 in alignment members 46.

Numerous screws and bolts hold the various parts of the apparatus together as clearly shown and their description is not necessary for a full understanding of the invention.

The operation of the present invention will be further explained. The apparatus should first be firmly positioned on a flat level surface. The handle 56 is then raised to its uppermost position. The test tube holder assembly 20 is engaged onto the slide bar 18 in base 12 with the desired test tube holes 76 or 78 positioned on the side of holder assembly 20 away from the vertical frame member 16. In the illustrated embodiment, up to three test tubes 26 with closures 28 ma be inserted into the desired holes 76 or 78 so that up to three pump mechanisms 38 may be simultaneously inserted.

After the test tube holder assembly 20 is engaged and positioned against the vertical frame member 16, the test tubes 26 including closures 28 are inserted into the desired test tube holes. One or more pump mechanisms 38 may be placed as shown by arrow 92 into pump support assembly 34 with needles 40 extending into a styrofoam block 94 which provides a convenient and safe means of handling pump mechanisms 38 to place them in pump support assembly 34. After the pump mechanisms 38 are in place, the styrofoam block 94 is removed, exposing the needles 40, and with the test tube holder assembly 20 containing sealed test tubes 26 in position at a first station 36, handle 56 is then pulled down fully, putting pressure on the pump support assembly 34 and thereby pushing the needles 40 of pump mechanisms 38 through the test tube closures 28.

After the insertion is completed, handle 56 is pulled up until the insertion mechanism adjustment screw 42 moves into a first detent position in notch 48 where the pump support assembly 34 has moved up some distance, thus releasing the pressure on the tubes 26 and closures 28. Now the test tube holder assembly 20 may be gently pulled forwardly, in a direction away from vertical frame member 16, to disengage the now attached pump mechanisms 38 from pump support assembly 34. The test tubes 26 and closures 28, with pump mechanisms 38 attached, can now be removed from holder assembly 20. Alternately, the test tube holder assembly 20 can be removed from slide bar 18, turned 180 degrees and remounted on slide bar 18, in order to attach pump mechanisms to any test tubes in the second row of holes.

The foregoing is a complete description of a preferred embodiment of the present invention. Numerous changes, modifications and improvements may be made without departing from the spirit and scope of the present invention. The present invention, therefore, should be limited only by the following claims.

What is claimed is:

1. A manually operated apparatus for attaching pump mechanisms to sealed test tubes, each test tube sealed by a resilient, puncturable closure, comprising:
    a frame including a base;
    support means attached to said frame for releasably supporting one or more pump mechanisms;
    means for releasably holding at least one test tube, said holding means movably engaging and being displaceable on the base of said frame into position in alignment with the support means; and
    manually operated insertion means, attached to said frame, for displacing said support means and the pump mechanisms supported thereon towards said holding means and test tubes held therein, wherein said support means holds said pump mechanisms to thereby puncture the closures of the test tubes with said pump mechanisms upon operation of said insertion means.

2. The apparatus of claim 1, wherein said insertion means comprises a handle, said handle movably attached at one end thereof to said frame; and
    wherein said support means comprises a pressure bar coupled to said handle, said pressure bar applying pressure via the pump mechanisms to the closures of the test tubes when said pressure bar is displaced by moving said handle thereby causing the pump mechanisms to puncture the closures of the test tubes.

3. The apparatus of claim 1, wherein said base includes a slide bar which slidably engages the holding means for positioning said holding means in alignment with said support means.

4. The apparatus of claim 3, wherein said holding means is removeable from said slide bar.

5. The apparatus of claim 1, wherein said support means includes means for adjusting alignment of said support means so that pump mechanisms held therein are centered relative to the closures of test tubes when said holding means is positioned in alignment with said support means.

6. The apparatus of claim 2, wherein said insertion means further comprises detent means for defining at least one preset position of said handle.

7. A method of using the apparatus of claim 1, comprising the steps of:
    placing at least one test tube having closures into the holding means;
    displacing the holding means into alignment with the support means;
    placing one or more pump mechanisms in said support means; and
    manually activating the insertion means to puncture the closures with pump mechanisms.

8. The method of claim 7, further comprising:
    displacing the holding means away from the support means after puncture of the closures; and
    removing the test tubes from the holding means.

9. The method of claim 7, wherein the insertion means includes a handle and the step of manually activating comprises pulling the handle.

10. The apparatus of claim 1, wherein the holding means comprises means for adapting the holding means to accommodate test tubes of different lengths and diameters.

11. A manually operated apparatus for inserting pump mechanisms into test tube closures, comprising:
    a frame including a rectangular base having a plurality of feet and including a slide bar attached to a surface of the base and extending parallel to the base across the center thereof, a vertical frame member having a first end attached to said slide bar adjacent to one end of said slide bar and extending perpendicular to said slide bar, a right-triangular shaped support member attached perpendicularly to said slide bar and to said vertical member adjacent the attached ends thereof, and at least one rectangular alignment support having at least one detent notch, said rectangular alignment support being attached to said vertical frame member at a distance from the end of said vertical support member that is attached to said slide bar;

an insertion mechanism attached to said vertical frame member at an end opposite said slide bar by a frame, and including a U-shaped bracket having holes for supporting a movable rod, the rod being movably attached at one end thereof by a first joint to a strut, the strut being movably connected to a handle bracket by a second joint, the handle bracket being movably connected at an end thereof to said first frame by a third joint and being attached to a handle, the handle when pulled causing said strut to move said rod towards said slide bar;

a pump mechanism support assembly for removably supporting one or more pump mechanisms thereon and including a detent screw, the pump mechanism support assembly being attached to one end of said rod to be moved along the length of said rectangular alignment support by movement of said rod, the detent screw extending through a pressure bar in slidable contact with said at least two rectangular alignment supports and said at least one detent notch; and a test tube holder removably and slidably attached to said slide bar for holding and positioning test tubes in axial alignment parallel to the pump mechanisms supported in said pump mechanism support assembly so that when the rod moves towards said slide bar the pump mechanisms are inserted into closures of the test tubes.

12. The apparatus of claim 1 wherein:
said support means releasably supports at least two pump mechanisms;
said holding means releasably holds at least two test tubes; and
said insertion means for puncturing the closures of each of two test tubes with a respective pump mechanism substantially simultaneously.

13. The apparatus of claim 1 wherein said insertion means applies a cantilever force to said support means for displacing said support means.

14. A manually operated apparatus for attaching pump mechanisms to sealed test tubes, each test tube sealed by a resilient, puncturable closure, comprising:
a frame including a base;
support means attached to said frame for releasably supporting one or more pump mechanisms;
means for releasably holding at least one test tube, said holding means movably engaging and being displaceable on the base of said frame into position in alignment with the support means, each test tube having an elongated axis; and
manually operated insertion means, attached to said frame, for applying a force to said support means along an axis offset from said test tube elongated axis for displacing said support means and the pump mechanisms supported thereon towards said holding means and test tubes held therein, wherein said support means holds said pump mechanisms to thereby puncture the closures of the test tubes with said pump mechanisms upon operation of said insertion means.

* * * * *